US012721789B2

(12) United States Patent
Geosits et al.

(10) Patent No.: US 12,721,789 B2
(45) Date of Patent: Sep. 1, 2026

(54) APPARATUS FOR HOLDING A TUBE AND ASSOCIATED METHOD OF USE

(71) Applicant: EZYAID PTY LTD, Hamilton (AU)

(72) Inventors: Adam Nicholas Geosits, Singleton (AU); Jessica Anne Hay, Gloucester (AU)

(73) Assignee: EZYAID PTY LTD, Hamilton (AU)

( * ) Notice: Subject to any disclaimer, the term of this patent is extended or adjusted under 35 U.S.C. 154(b) by 705 days.

(21) Appl. No.: 18/020,838

(22) PCT Filed: Aug. 11, 2021

(86) PCT No.: PCT/AU2021/050880
§ 371 (c)(1),
(2) Date: Feb. 10, 2023

(87) PCT Pub. No.: WO2022/032339
PCT Pub. Date: Feb. 17, 2022

(65) Prior Publication Data

US 2023/0263707 A1 Aug. 24, 2023

(30) Foreign Application Priority Data

Aug. 11, 2020 (AU) ................................ 2020902829

(51) Int. Cl.
*A61J 15/00* (2006.01)
*A61M 25/02* (2006.01)

(52) U.S. Cl.
CPC ....... *A61J 15/0034* (2013.01); *A61J 15/0003* (2013.01); *A61M 2025/0226* (2013.01);
(Continued)

(58) Field of Classification Search
CPC .............. A61J 15/0034; A61J 15/0003; A61M 2025/0226; A61M 2025/0253; A61M 2205/583
(Continued)

(56) References Cited

U.S. PATENT DOCUMENTS 3,918,446 A * 11/1975 Buttaravoli ........... A61M 25/02
128/DIG. 26
4,738,662 A 4/1988 Kalt
(Continued)

FOREIGN PATENT DOCUMENTS

EP 3693050 A1 8/2020
GB 2251796 A 7/1992
(Continued)

*Primary Examiner* — Phillip A Gray
(74) *Attorney, Agent, or Firm* — Dickinson Wright PLLC; Andrew D. Dorisio

(57) ABSTRACT

An apparatus and method for fitting a tube to a user, preferably but not exclusively for the face of the user. The apparatus comprises an elongate body including a first and second portion, the portions connected at a fold-line; the first portion including a first and second side; the second portion including a third and fourth side; wherein the first side and the third side are at least partially coated in a first adhesive; wherein the second side is at least partially coated in a second adhesive; and wherein the first adhesive provides a higher level of adhesion compared to the second; and wherein upon folding, the second and third sides face each other.

19 Claims, 6 Drawing Sheets

(52) U.S. Cl.
CPC ............... *A61M 2025/0253* (2013.01); *A61M 2205/583* (2013.01)

(58) Field of Classification Search
USPC ............................................................ 604/73
See application file for complete search history.

(56) References Cited

U.S. PATENT DOCUMENTS

| | | | | |
|---|---|---|---|---|
| 9,827,396 | B2 * | 11/2017 | Souza .................. | A61M 25/02 |
| 2016/0346495 | A1 | 12/2016 | Payton | |

FOREIGN PATENT DOCUMENTS

| | | | |
|---|---|---|---|
| WO | 2013157960 | A1 | 10/2013 |
| WO | 2014149668 | A1 | 9/2014 |
| WO | 2015031953 | A1 | 3/2015 |
| WO | 2016148585 | A1 | 9/2016 |
| WO | 2017034907 | A1 | 3/2017 |
| WO | 2018134744 | A1 | 7/2018 |

* cited by examiner

APPARATUS FOR HOLDING A TUBE AND ASSOCIATED METHOD OF USE

TECHNICAL FIELD

The present disclosure relates to an apparatus for holding a tube, for example a nasoenteral tube to the face of a user, and a method of fitting a tube to the face of a user using said apparatus.

BACKGROUND OF THE DISCLOSURE

Many medical conditions require the fitting of a tube to the face of a user for an extended period of time, the tube typically being used to supply at least one of oxygen, airflow, nutrients or medications to the user. These medical tubes may also be used for other procedures, for example to remove the contents of the user's stomach. These tubes are usually fitted to the user for extended periods of time.

A number of these tubes are designed to be inserted through the nostril of a user, such as nasal cannulae (terminating within the nasal cavity), as well as nasoenteral tubes including nasogastric, nasoduodenal and nasojujenal tubes (extending through the oseophagus into the stomach, duodenum, and jujenum respectively). Other medical tubes, for example osoenteral tubes, are still fitted to the face of a user but are instead inserted through the mouth rather than through the nostril. Further medical tubes, for example gastrostomy and jujunostomy tubes, tubes for parenteral nutrition, and various types of cannulae and catheters are attached to the skin of a user (on the torso, chest or arms for example) for extended periods of time.

Of the nasoenteral tubes, nasogastric tubes are the most common. A typical process of fitting a nasogastric tube to the face of a user includes: applying a layer of a hydrocolloid dressing such as DuoDERM™ to the user's cheek to protect the skin; inserting the nasogastric tube into the user's nasal passage to the correct insertion measurement; placing a piece of tape onto the user's nasogastric tube to hold the tube at the insertion level; checking the tube is in the correct position by any suitable measurement, for example by drawing back with a syringe and testing the pH of the aspirate with litmus paper or another suitable method; and either adjusting the position of the tube or securing the tube with two more pieces of tape if it is in the correct location. Other nasoenteral tubes follow similar methods, though fitting of these other tubes is typically carried out by medical professionals in a hospital environment.

Ideally, the fitting process is carried out by two people, with a first person holding the tube and a second person cutting and fitting the tape to the user. Commonly however, a single person must adjust and test the tube by themselves. This is commonly the case when the fitting is being carried out at home rather than in a hospital setting. In these situations, the person fitting the tube may be a parent or carer rather than a medical professional. Particularly when the intended user is an infant or child, they may become uncomfortable and agitated during this process. A further issue is that the tape typically must be changed at least two times a week as it soils, becomes ineffective and lifts up from the user's face, increasing the required frequency of tube fittings. Additionally, the present method requires at least two pieces of tape on different angles to shape to the face of the user. Other tubes, not fitted to the face of a user, are usually held in place with one or more strips of tape, typically in a transverse direction to the lengthways direction of the tube.

Another shortcoming of the present methods is that the user (again in particular when an infant or child) is often able to dislodge the tube from its correct position. The consequences of an improperly positioned tube range from irritation and discomfort to the user to more serious outcomes, including causing an oral aversion to develop or death. As an example, an improperly positioned nasoenteric tube may instead terminate in the lungs and cause damage to the respiratory system or infections such as pneumonia via food/medicaments entering the lungs. For infants and children, the discomfort of the tube may cause them to grasp and pull on the tube, dislodging both the tube and tape from the face of the user as well as altering the inserted depth of the tube.

There thus exists a need to find a method for fitting a tube to a user, preferably but not exclusively for fitting a tube to the face of the user, which can be easily carried out by a single person, as well as an apparatus/method which can hinder the ability of the user to accidentally dislodge the tube when in place and overcome the present shortcomings of present methods by providing reduced soiling and/or frequency of changing. The present invention seeks to provide an apparatus and method which at least partially achieves these aims.

SUMMARY OF THE INVENTION

In one broad aspect, there is provided an apparatus for securing a tube to a face of a user, the apparatus comprising: an elongate body including a first and second portion, the portions connected at a fold-line; the first portion including a first and second side; the second portion including a third and fourth side; wherein the first side and the third side are at least partially coated in a first adhesive; wherein the second side is at least partially coated in a second adhesive; and wherein the first adhesive provides a higher level of adhesion compared to the second; and wherein upon folding, the second and third sides face each other.

In certain embodiments, at least one of the first, second, third and fourth side is covered with a removable protective layer prior to use.

In certain embodiments, the removable protective layer is a release liner.

In certain embodiments, the release liner comprises a paper substrate with a silicone release agent.

In certain embodiments, there are a plurality of release liners and each release liner includes a representation of a number indicating the order in which the release liners should be removed when fitting the tube to the face of the user.

In certain embodiments, the elongate body is made from a thermoplastic polyurethane or elastomer.

In certain embodiments, the first adhesive is an acrylic or synthetic rubber pressure sensitive adhesive.

In certain embodiments, the second adhesive is selected from at least one of a silicone adhesive, polyurethane film, or acrylic pressure sensitive adhesive.

In certain embodiments, the first portion is dimensioned to have a smaller surface area than the second portion.

In certain embodiments, the first portion is dimensioned to have a width which is approximately half the width of the second portion.

In certain embodiments, the ratio of first portion length: second portion length is between 0.90 to 1.

In certain embodiments, the fold-line extends in a direction substantially perpendicular to the main lengthwise direction of the elongate body.

In certain embodiments, at least one of the first and second portions narrows in width towards an end opposing the fold-line to provide a nose fitting region when applied to the user's face.

In certain embodiments, at least one of the first and second portion narrows in width towards the fold-line.

In certain embodiments, the tube is a nasal-gastric tube.

In a second broad aspect, there is provided a method for applying an apparatus for securing a tube to a face of a user, wherein the apparatus comprises: an elongate body including a first and second portion, the portions connected at a fold-line; the first portion including a first and second side; the second portion including a third and fourth side; wherein the first side and the third side are at least partially coated in a first adhesive; wherein the second side is at least partially coated in a second adhesive; and wherein the first adhesive provides a higher level of adhesion compared to the second; and wherein upon folding, the second and third sides face each other; the method comprising: applying the first side between a nose and ear of the face of the user; positioning a tube on the second side of the first portion; folding the elongate body at the fold-line so that the third side is brought into contact with at least one of the tube, second side, and face of the user.

In a third broad aspect, there is provided a method for applying an apparatus for securing a tube to a face of a user, wherein the apparatus comprises: an elongate body including a first and second portion, the portions connected at a fold-line; the first portion including a first and second side; the second portion including a third and fourth side; wherein the first side and the third side are at least partially coated in a first adhesive; wherein the second side is at least partially coated in a second adhesive; and wherein the first adhesive provides a higher level of adhesion compared to the second; and wherein the first, second, and third sides are covered with a removable protective layer; the method comprising: removing the protective layer from the first side; applying the first side between a nose and ear of the face of the user; removing the protective layer from the second side; positioning a tube on the second side of the first portion; removing the protective layer from the third side; folding the elongate body at the fold-line so that the third side is brought into contact with at least one of the tube, second side, and face of the user.

In certain embodiments of the second and third aspects, the apparatus is an apparatus according to any one of the first aspect.

In a fourth aspect, there is provided an apparatus for securing a tube to the skin of a user, the apparatus comprising: an elongate body including a first and second portion, the portions connected at a fold-line; the first portion including a first and second side; the second portion including a third and fourth side; wherein the first side and the third side are at least partially coated in a first adhesive; wherein the second side is at least partially coated in a second adhesive; and wherein the first adhesive provides a higher level of adhesion compared to the second; and wherein upon folding, the second and third sides face each other.

In certain embodiments of the fourth aspect, the apparatus is an apparatus according to the first aspect.

Other aspects, features, and advantages will become apparent from the following detailed description when taken in conjunction with the accompanying drawings, which are a part of this disclosure and which illustrate, by way of example, principles of the inventions disclosed.

BRIEF DESCRIPTION OF THE FIGURES

The present disclosure will become better understood from the following detailed description of various non-limiting embodiments thereof, described in connection with the accompanying figures, wherein.

DETAILED DESCRIPTION

In the following description, embodiments will be described in reference to a nasogastric tube. It will be understood that the apparatus may also be used for other types of medical tubes inserted through the nostril such as nasojujenal tubes, nasoduodenal tubes, and nasal cannuale, as well as those inserted through other orifices of a user's face, such as osoenteral tubes. The apparatus may also be suited to use in sleep studies where tubing in the form of nasal cannula and/or wiring connected to electrodes are attached to the user's face and body for the duration of the study. It will be further understood that other embodiments may be adapted for medical tubes fitted to other parts of a user's body, for example the limbs or torso. In these instances, the tube may be inserted through a stoma or other opening created by a medical professional. Another instance where embodiments of the apparatus may be especially applicable is the insertion of intravenous cannulae, which must be connected to the user for extended periods of time through a vein such as in the arm. Further, it will be understood that a variety of medical tubes are also used in the veterinary profession in similar applications such as enteral feeding, and so further embodiments may be adapted for circumstances where the user is not a human but an animal for fitting by a veterinary professional.

Figure 1A:
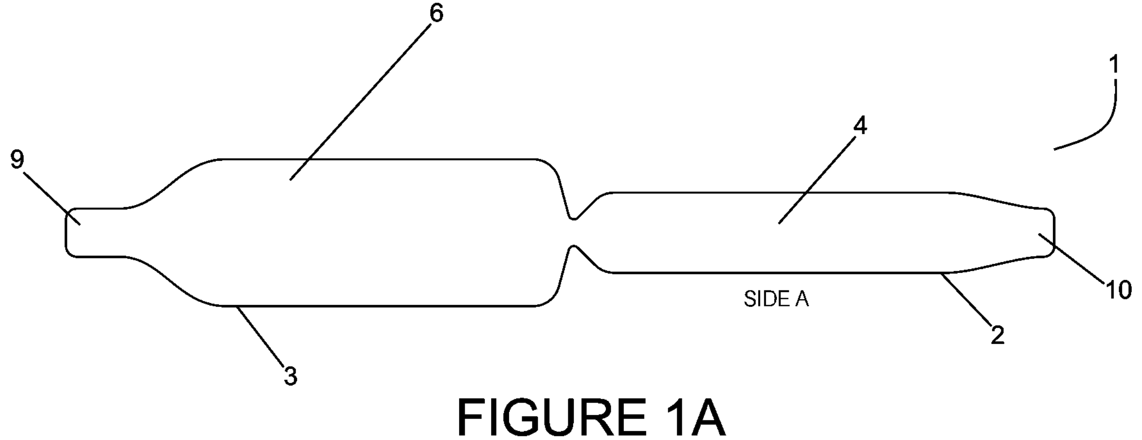
FIG. 1A shows an embodiment of the apparatus.
Figure 1B:
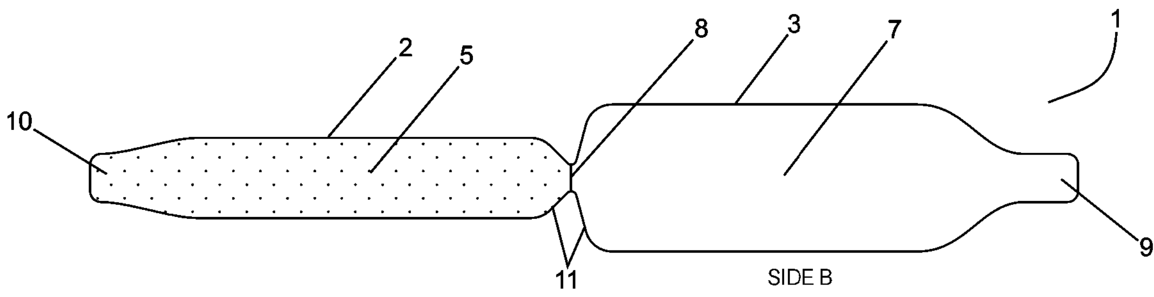
FIG. 1B shows the reverse side of the apparatus of FIG. 1A.

As shown by the embodiment in FIGS. 1A and 1B, the apparatus 1 consists of an elongate body which can be thought of as consisting of two portions: a first portion 2 and a second portion 3. In another way of thinking, the first portion 2 may be thought of as an inner portion and the second portion 3 may be thought of as an outer portion or cover. The term elongate body is intended to be understood as referring to the entire body (both portions 2 and 3) of the apparatus 1, and to a shape wherein the body extends substantially further in a first direction (referred to as the lengthways direction) than in a second direction which is approximately 90° from the first direction (also referred to as the transverse direction).

The first or inner portion 2 has a first side 4 which in use is placed in contact with the skin of a user between the nose/mouth and ear. In the embodiments shown in these figures, the user is a human, in particular a child. It will be understood that in other embodiments, the user may be a human adolescent or adult, or even an animal. The first portion 2 also has an opposite side 5 which in use contacts the tube. The second portion or cover 3 has a first side 7 which in use contacts both the skin of the user and the tube, as well as an opposite side 6 which faces away from the skin of a user when in use.

The two portions are attached to each other at a fold-line 8 on which the second portion 3 is folded so that it covers the first portion 1 when fitting a tube to the face of a user. In this embodiment, the axis of the fold-line extends in a direction perpendicular to the main lengthways direction of the elongate body, and the first and second portions are attached to each other at this fold line. In this embodiment, the second portion 3 is dimensioned to have a greater surface area than the first portion 2. Particularly, the length in the main lengthways direction of the first portion is approximately between 90-100% of the length of the second portion, and the width of the first portion is approximately half the width of the second portion, when both are taken at their widest points.

Both the first portion 2 and the second portion 3 in this embodiment include a nose fitting region 10 and 9 respectively. These consist of a narrowing in width towards the outer end of the portion in a direction away from the fold-line 8. In use, this reduction in width allows the nose fitting region to be positioned at least partially below the nostril of the user, allowing the tube to be covered over a greater length than otherwise possible. Preferably, as shown in this embodiment, the narrowing occurs on both lengthwise sides so that the benefits of the nose-fitting region can be achieved when the apparatus is applied to either/both the left or right side of the user's face.

In this embodiment, both portions also narrow towards the fold-line in a tube holding region 11. Similar to the nose fitting portion, this allows the tube to be covered over a greater region than would otherwise be possible. Additionally in this embodiment, when the apparatus 1 is bent along the fold-line 8, a v-shaped recess is formed which can support the tube while it is being adjusted and fitted to the correct insertion depth. Preferably, the sides narrow on both sides to allow the placement of the apparatus on either/both sides of the user's face. In other embodiments, the two portions may instead be attached to each other at another point and the tube may be supported entirely by the adhesion of the tube to side 5 rather than in conjunction with a v-shaped recess formed by the two portions.

Preferably, the elongate body is made from a thermoplastic polyurethane or polyethylene material. In some embodiments, the material may be micro-perforated so that the material is breathable and thus more comfortable for the user. Sides 4 and 7 of the first and second portions 2 and 3 are coated or otherwise impregnated with an adhesive surface suitable for use on the skin of a patient. For example, the adhesive may be a pressure sensitive adhesive such as an acrylic or synthetic rubber adhesive. Side 5 of the apparatus contains a different adhesive with a lower level of adhesion than the adhesive on sides 4 and 7, such as a silicone adhesive. Side 6 is not coated or otherwise impregnated with an adhesive, although in some embodiments it may include an additional layer of the thermoplastic polymer material. In a particularly preferred embodiment, side 5 is formed of at least one of 40 gsm acrylic PSA, 100 um polyurethane film, and/or 150 gsm silicone. It will be understood, however, that the chosen adhesives for sides 4 and 7, and for side 5 may vary. It is important, however, that the adhesive on side 5 provides a lower level of adhesion compared to sides 4 and 7.

Figure 2A:
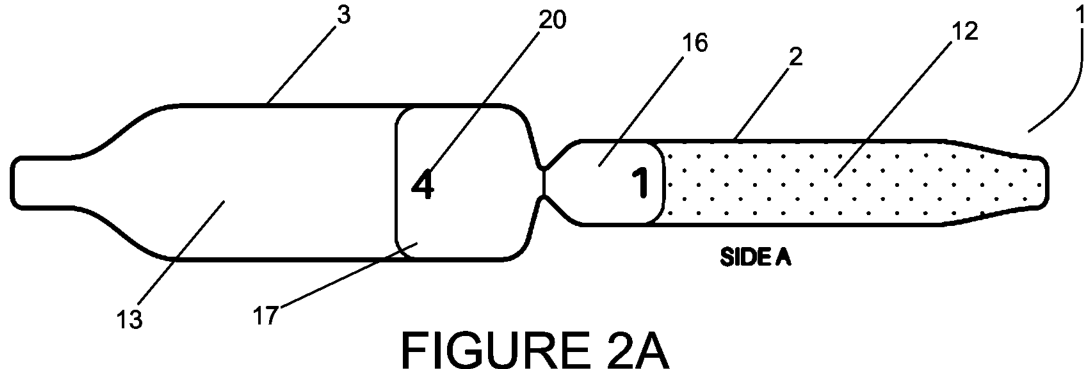
FIG. 2A shows another embodiment of the apparatus.
Figure 2B:
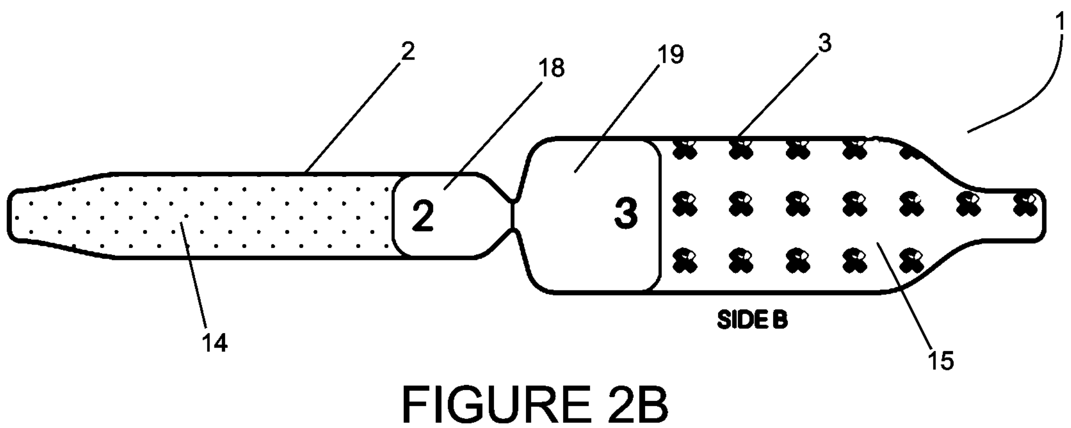
FIG. 2B shows the reverse side of the apparatus of FIG. 2A.

An embodiment is shown in FIGS. 2A and 2B where release liners 12, 13, 14, 15 have been applied to both sides of the first and second portions 2 and 3. In this embodiment, the release liner is in the form of bleached craft paper with a silicone release on the apparatus facing side to facilitate easy removal from the surfaces of the sides. The release liners are shaped to have the same dimension as the portion of the apparatus they are applied to. These release liners both maintain the tack of the adhesives prior to use and provide a firm structure to the apparatus prior to use. Structurally, the release liners allow the elongate body 1 to be made from a thin film of thermoplastic polyurethane or similar without the risk of the body folding in and adhering to itself incorrectly. Providing a thin film is advantageous as it reduces both the weight and the distance the apparatus extends from the user's face, making the apparatus more comfortable for the user to wear. In preferred embodiments, side 6 which does not have an adhesive surface applied to it, is not provided with a release liner.

The release liners 12, 13, 14, 15 are each provided with a pull-tab 16, 17, 18, 19 to allow the person fitting the tube to more easily remove the release liners. In this embodiment, the pull-tab is shaped as a partial reflection of the shape of the release liner, and folded back on the release liner at the same location as the fold-line 8 of the elongate body. These pull tabs may optionally include a graphical representation of numbers 20 which indicate the order in which the release liners should be removed when fitting the apparatus to the face of a user, further increasing the ease of use by a non-medical professional and training of such a person by a medical professional.

Figure 3:
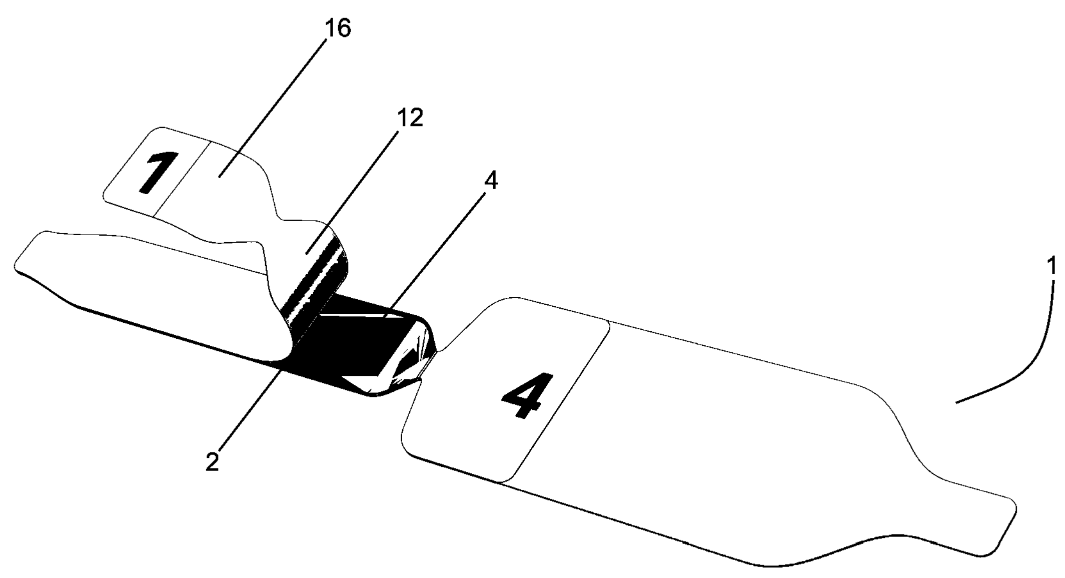
FIG. 3 shows the first step in fitting an embodiment of the apparatus to the face of a user.

FIG. 3 shows the first step in applying an embodiment of the apparatus to the face of a user. A pull tab 16 marked with a '1' is pulled up and away from the elongate body 1 to remove release liner 12 and reveal a first side 4 of the first portion 2.

Figure 4:
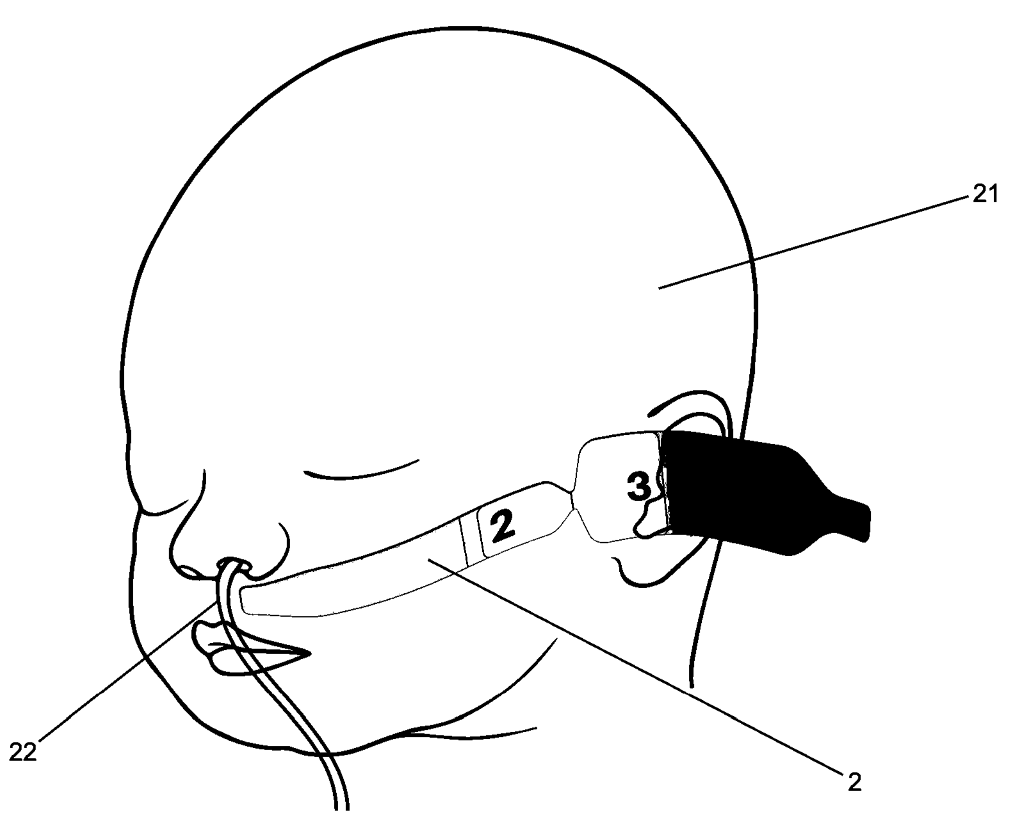
FIG. 4 shows the second step in fitting an embodiment of the apparatus to the face.

FIG. 4 shows the second step in applying an embodiment of the apparatus to the face of a user 21 with medical tube, in this case a nasogastric tube 22. The exposed first side 4 of first portion 2 is positioned between a nose and ear of the user and pressure is applied to adhere the first side to the skin of the user.

Figure 5:
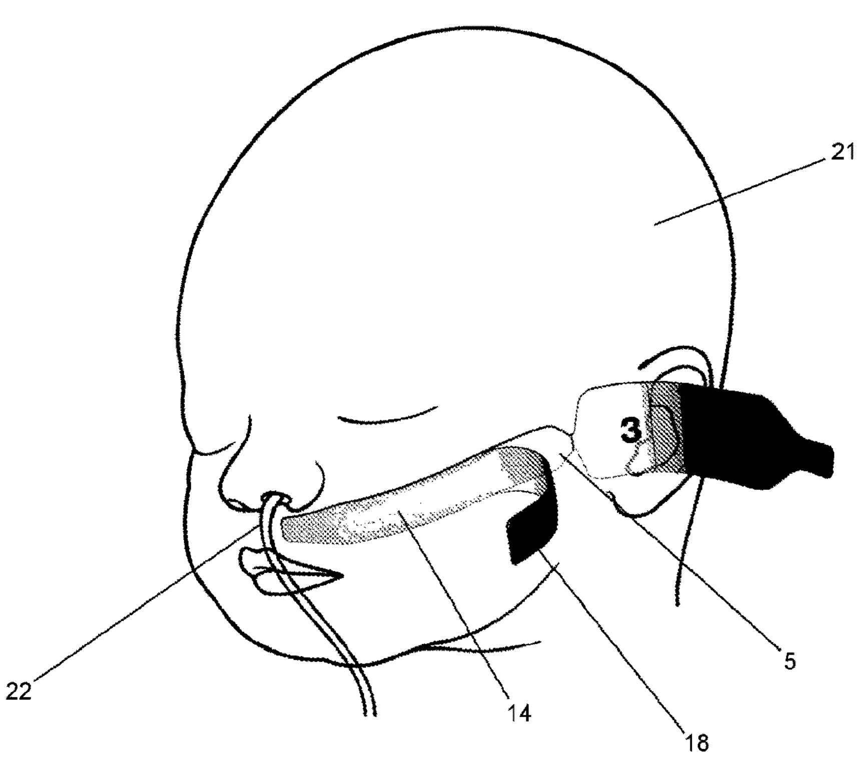
FIG. 5 shows the third step in fitting an embodiment of the apparatus to the face.

FIG. 5 shows the third step in applying an embodiment of the apparatus, where pull tab 18 is pulled up and away to expose side 5 of the first portion. Pull tab 18 in this embodiment is marked with the number '2' to indicate to the person applying the apparatus that it should be removed following removal of pull tab 16 and application to the face of the user.

Figure 6:
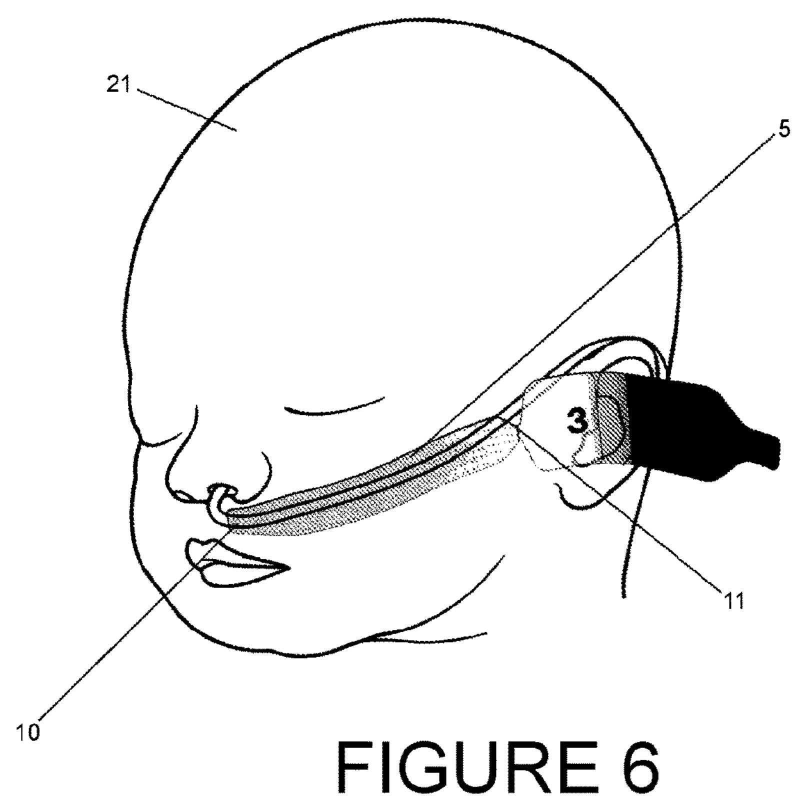
FIG. 6 shows the fourth step in fitting an embodiment of the apparatus to the face.

FIG. 6 shows the fourth step, where the tube 22 is placed across the side 5 of the first portion and brought over the tube holding region 11 and over the ear of the user. This figure clearly shows the v-shaped recess formed by tube holding region 11 which is present in this embodiment. FIG. 6 also shows how the nose fitting region 10 can be placed at least partially under the nostril of the user 21. At this point, the tube can be easily tested and repositioned as the surface of side 5 comprises a silicone adhesive with relatively low initial tack, the relatively small surface area of contact between the tube and side 5, and the tube holding region 11, allow the tube to remain in place while being tested/repositioned. Further, the level of tack of side 5 is balanced against the adhesion to the skin of the user of side 4 so that pulling the tube off the apparatus does not pull the apparatus from the face of the user, owing to the higher level of adhesion on side 4 relative to side 5.

Figure 7:
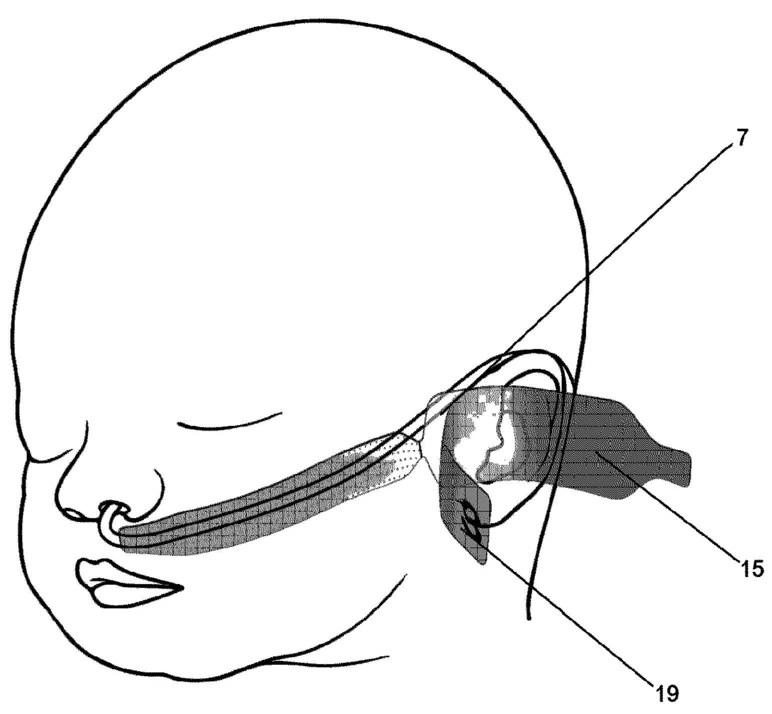
FIG. 7 shows the fifth step in fitting an embodiment of the apparatus to the face.

FIG. 7 shows the fifth step, where pull tab 19 is pulled up and away from elongate body to remove release liner 15 to reveal side 7. Pull tab 19 is marked with the numeral '3' to aid the person applying the apparatus in removing the pull tabs in the correct order.

Figure 8:
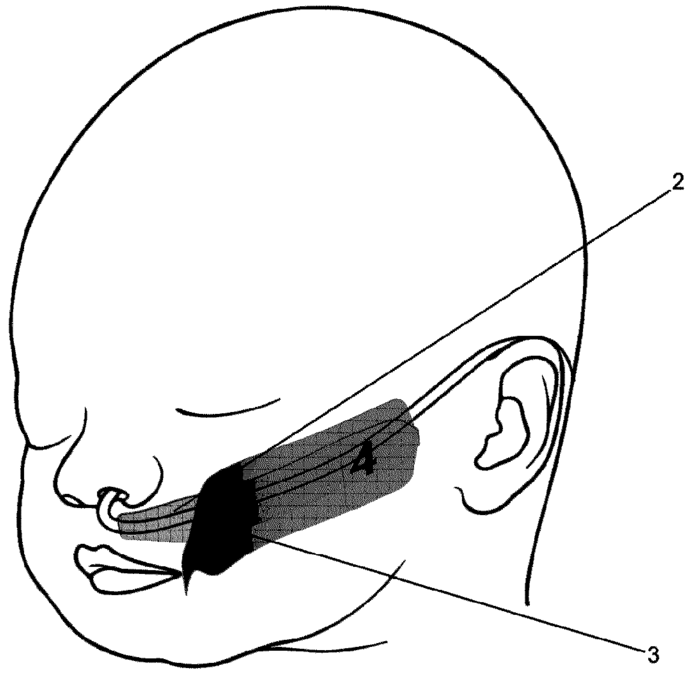
FIG. 8 shows the sixth step in fitting an embodiment of the apparatus to the face.

FIG. 8 shows the sixth step, where the second portion 3 is folded over first portion 2 to cover both the first portion and tube. As the second portion has a larger surface area than the first portion, the second portion also comes into contact with the skin of the user both above and below where the first portion is attached to the skin of a user. Pressure is applied to the second portion in the direction of the user's face so that the portion adheres to at least one of the face of the user, tube and first portion.

Figure 9:
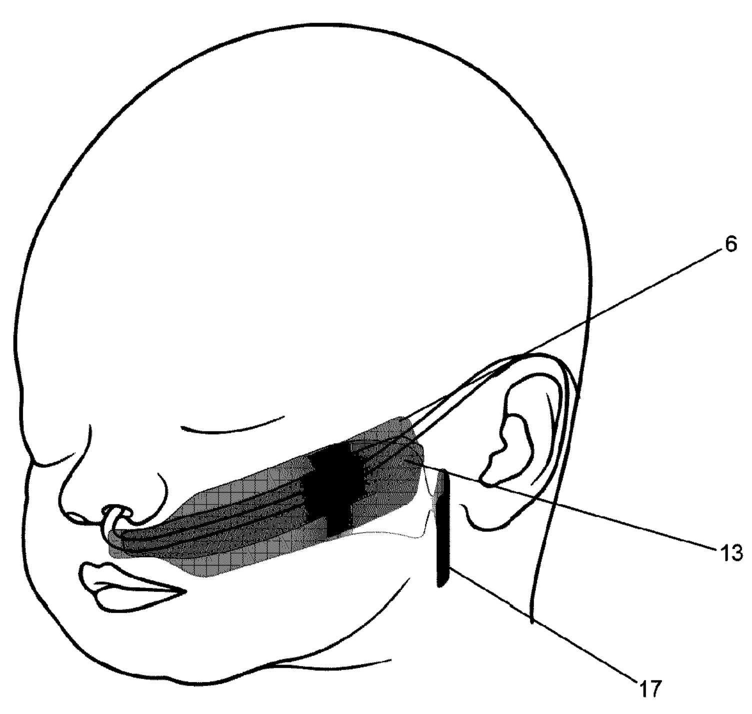
FIG. 9 shows a seventh step in fitting an embodiment of the apparatus to the face.

FIG. 9 shows the seventh step, where pull tab 17 is pulled up and away, separating the release liner 13 from the side 6. By retaining release liner 13 until this final step, the second portion remains flat and stiff, preventing the second portion from folding back over itself or losing its shape prior to the second portion adhering to the tube/first portion/skin of the user. Said pull tab is marked with the numeral '4' to indicate that it should be removed following all other pull tabs so as to maintain the stiffness of the second portion until this point. It will be understood that in other embodiments, the fourth release liner 13 is not present, and instead the structural support is entirely provided by the third release liner 15.

Figure 10:
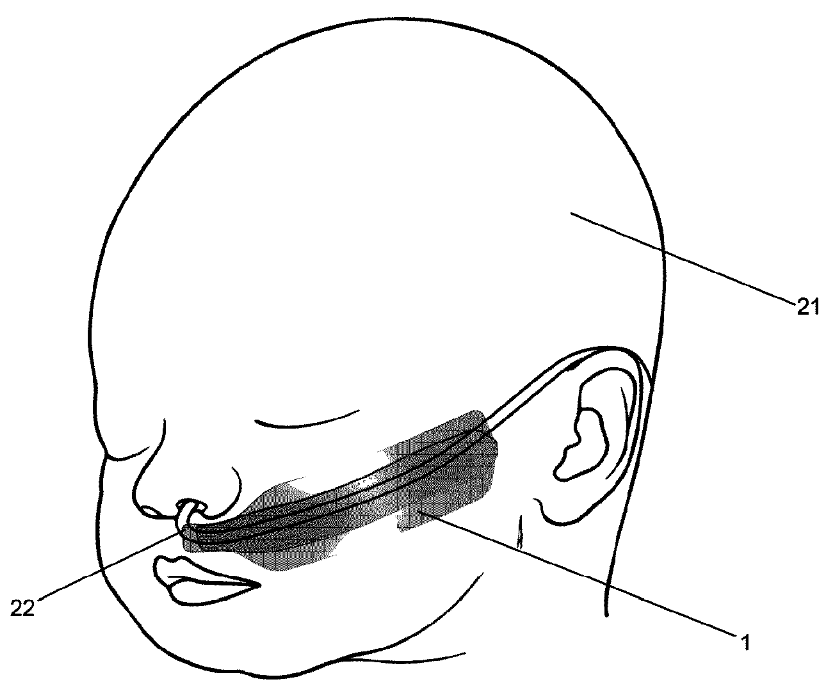
FIG. 10 shows the apparatus in position on the face of a user.

FIG. 10 shows the apparatus 1 in use on the face of a user 21 so that tube 22 is covered for a substantial distance between the nostril and ear of a user. This makes it harder for the user to grasp and pull the tube, possibly dislodging it from the correct position.

In some embodiments, at least part of the apparatus is transparent or otherwise see-through, so that the tube may be visually inspected and any problems such as blockages identified without having to remove or replace the apparatus. Transparent or see-through material may also be more aesthetically pleasing for the user as the apparatus may be less visually apparent compared with tape. In other embodiments, the apparatus may be made of a coloured or patterned material, or with a graphic, design and/or branding printed or otherwise applied to the body of the apparatus.

The apparatus may be available in a variety of sizes to fit different users. For example, the apparatus may be available in three sizes for different age groups: adults, toddler to early teens, and premature/newborns to infants, wherein the length of the elongate body is adapted to fit a typically sized face for each group. In other embodiments, more or fewer sizes may be available.

As the tube is covered and held against the user's face for the majority of the distance between the nostril and ear, it is far harder for the tube to become dislodged or grasped and pulled by the user compared with existing methods. This may also reduce instances of a known problem with existing tube holding methods where constant refitting/adjustment of the tube causes an oral aversion, or a fear/reluctance to eat and drink, to develop in the user, in particular when the user is a newborn or child. Oral aversion can lead to a number of negative health outcomes for the user, such as poor growth and/or consistent distress. The present apparatus is both harder to dislodge and requires less frequent changing, lessening the traumatic/distressing elements of intubation for the user.

The design of the apparatus provides a number of advantages compared to the present methods of fitting the tube to the face of a user with tape. While due to soiling and movement, the tape must be replaced on average around two times a week, the present apparatus can be left in place for between five to seven days, although it may sometimes be changed more frequently, for example in a hospital setting, the apparatus may be changed every three days. Additionally, it is far easier for a single person to fit a tube to the face of a user compared to cutting and measuring tape to fit the user's face. A further benefit of reducing the frequency of changing the apparatus, in particular when used in the treatment of infectious diseases (for example to hold a respiratory tube in a patient suffering from COVID-19), is that the contamination risk to the patient and infection risk to the person applying the apparatus is reduced relative to existing methods.

Additionally, the present apparatus is optimized for easy mass manufacture. The materials and design allow production to be carried out predominantly using film lamination and rotary die cutting.

Throughout this description, the reference to a tube is intended as encompassing substantially tube-shaped medical/veterinary paraphernalia such as wiring/cabling for electrodes or other sensors, which may be attached to the body of a user for an extended period of time in a similar fashion to medical/veterinary tubing, such as but not limited to nasal/intravenous cannulae and nasoenteral tubes.

In the foregoing description of certain embodiments, specific terminology has been resorted to for the sake of clarity. However, the disclosure is not intended to be limited to the specific terms so selected, and it is to be understood that each specific term includes other technical equivalents which operate in a similar manner to accomplish a similar technical purpose.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The reference in this specification to any prior publication (or information derived from it), or to any matter which is known, is not, and should not be taken as, an acknowledgement or admission or any form of suggestion that prior publication (or information derived from it) or known matter forms part of the common general knowledge in the field of endeavour to which this specification relates.

In addition, the foregoing describes only some embodiments of the invention(s), and alterations, modifications, additions and/or changes can be made thereto without departing from the scope and spirit of the disclosed embodiments, the embodiments being illustrative and not restrictive.

Furthermore, invention(s) have described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention(s). Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment.

The invention claimed is:

1. An apparatus for securing a tube to a face of a user, the apparatus comprising:

an elongate body including a first portion and a second portion, the first portion and the second portion connected at a fold-line;

the first portion including a first side adapted for placement in contact with skin of the user in use and a second side adapted for placement in contact with the tube in use;

the second portion including a third side adapted for placement in contact with the skin of the user and the tube in use and a fourth side adapted to face away from the skin of the user in use;

wherein the first side and the third side are at least partially coated in a first adhesive;

wherein the second side is at least partially coated in a second adhesive;

wherein the first adhesive provides a higher level of adhesion compared to the second adhesive; and wherein upon folding, the second and third sides face each other.

2. The apparatus of claim 1, wherein at least one of the first, second, third and fourth side is covered with a removable protective layer prior to use.

3. The apparatus of claim 2, wherein the removable protective layer is a release liner.

4. The apparatus of claim 3, wherein the release liner comprises a paper substrate with a silicone release agent.

5. The apparatus of either claim 3, wherein there are a plurality of release liners and each release liner includes a representation of a number indicating the order in which the release liners should be removed when fitting the tube to the face of the user.

6. The apparatus of claim 1, wherein the elongate body is made from a thermoplastic polyurethane or elastomer.

7. The apparatus of claim 1, wherein the first adhesive is an acrylic or synthetic rubber pressure sensitive adhesive.

8. The apparatus of claim 1, wherein the second adhesive is selected from at least one of a silicone adhesive, polyurethane film, or acrylic pressure sensitive adhesive.

9. The apparatus of claim 1, wherein at least one of the first portion and second portion are at least partially transparent.

10. The apparatus of claim 1, wherein the first portion is dimensioned to have a smaller surface area than the second portion.

11. The apparatus of claim 10, wherein the first portion is dimensioned to have a width which is approximately half the width of the second portion.

12. The apparatus of claim 10, wherein the ratio of first portion length: second portion length is between 0.90 to 1.

13. The apparatus of claim 1, wherein the fold-line extends in a direction substantially perpendicular to the main lengthwise direction of the elongate body.

14. The apparatus of claim 13, wherein at least one of the first and second portions narrows in width towards an end opposing the fold-line to provide a nose fitting region when applied to the user's face.

15. The apparatus of claim 1, wherein at least one of the first and second portion narrows in width towards the fold-line.

16. The apparatus of claim 1, wherein the tube is a nasal-gastric tube.

17. A method for applying an apparatus for securing a tube to a face of a user, wherein the apparatus comprises:

an elongate body including a first portion and a second portion, the first portion and the second portion connected at a fold-line;

the first portion including a first side adapted for placement in contact with skin of the user in use and a second side adapted for placement in contact with the tube in use;

the second portion including a third side adapted for placement in contact with the skin of the user and the tube in use and a fourth side adapted to face away from the skin of the user in use;

wherein the first side and the third side are at least partially coated in a first adhesive;

wherein the second side is at least partially coated in a second adhesive;

wherein the first adhesive provides a higher level of adhesion compared to the second adhesive; and wherein upon folding, the second and third sides face each other;

the method comprising:

applying the first side between a nose and ear of the face of the user;

positioning a tube on the second side of the first portion;

folding the elongate body at the fold-line so that the third side is brought into contact with at least one of the tube, second side, and face of the user.

18. A method for applying an apparatus for securing a tube to a face of a user, wherein the apparatus comprises:

an elongate body including a first portion and a second portion, the first portion and the second portion connected at a fold-line;

the first portion including a first side adapted for placement in contact with skin of the user in use and a second side adapted for placement in contact with the tube in use;

second portion including a third side adapted for placement in contact with the skin of the user and the tube in use and a fourth side adapted to face away from the skin of the user in use;

wherein the first side and the third side are at least partially coated in a first adhesive;

wherein the second side is at least partially coated in a second adhesive;

wherein the first adhesive provides a higher level of adhesion compared to the second adhesive; and wherein the first, second, and third sides are covered with a removable protective layer;

the method comprising:

removing the protective layer from the first side;

applying the first side between a nose and ear of the face of the user;

removing the protective layer from the second side;

positioning a tube on the second side of the first portion;

removing the protective layer from the third side;

folding the elongate body at the fold-line so that the third side is brought into contact with at least one of the tube, second side, and face of the user.

19. An apparatus for securing a tube to skin of a user, the apparatus comprising:

an elongate body including a first portion and a second portion, the first portion and the second portion connected at a fold-line;

the first portion including a first side adapted for placement in contact with the skin of the user in use and a second side adapted for placement in contact with the tube in use;

the second portion including a third side adapted for placement in contact with the skin of the user and the tube in use and a fourth side adapted to face away from the skin of the user in use;

wherein the first side and the third side are at least partially coated in a first adhesive;

wherein the second side is at least partially coated in a second adhesive;

wherein the first adhesive provides a higher level of adhesion compared to the second adhesive; and wherein upon folding, the second and third sides face each other.

* * * * *